US010610264B2

(12) United States Patent
Petit

(10) Patent No.: US 10,610,264 B2
(45) Date of Patent: Apr. 7, 2020

(54) POLYAXIAL VERTEBRAL ANCHORING DEVICE FOR STRAIGHTENING A VERTEBRA

(71) Applicant: SAFE ORTHOPAEDICS, Eragny sur Oise (FR)

(72) Inventor: Dominique Petit, Verton (FR)

(73) Assignee: Safe Orthopaedics, Eragny sur Oise (FR)

( * ) Notice: Subject to any disclaimer, the term of this patent is extended or adjusted under 35 U.S.C. 154(b) by 0 days.

(21) Appl. No.: 15/520,436

(22) PCT Filed: Oct. 20, 2015

(86) PCT No.: PCT/FR2015/052817
§ 371 (c)(1),
(2) Date: Apr. 20, 2017

(87) PCT Pub. No.: WO2016/062963
PCT Pub. Date: Apr. 28, 2016

(65) Prior Publication Data
US 2017/0311988 A1    Nov. 2, 2017

(30) Foreign Application Priority Data
Oct. 20, 2014  (FR) .................... 14 60059

(51) Int. Cl.
*A61B 17/70*    (2006.01)
*A61B 17/86*    (2006.01)
(52) U.S. Cl.
CPC ...... *A61B 17/7037* (2013.01); *A61B 17/7034* (2013.01); *A61B 17/7038* (2013.01); *A61B 17/8605* (2013.01)

(58) Field of Classification Search
CPC .................. A61B 17/7038; A61B 17/7037
See application file for complete search history.

(56) References Cited

U.S. PATENT DOCUMENTS

| 5,989,254 A | 11/1999 | Katz | |
|---|---|---|---|
| 2006/0079894 A1* | 4/2006 | Colleran | A61B 5/103 606/86 A |

(Continued)

FOREIGN PATENT DOCUMENTS

| EP | 1923011 A1 | 5/2008 |
|---|---|---|
| FR | 2920959 A1 | 3/2009 |

OTHER PUBLICATIONS

International Search Report for PCT/FR2015/052817 dated Dec. 2, 2015.

*Primary Examiner* — Jan Christopher L Merene
(74) *Attorney, Agent, or Firm* — Bachman & LaPointe, P.C.

(57) ABSTRACT

A vertebral anchor device comprising a bone anchor screw having a screw body and a screw head for coupling a link element to the screw body, the screw head being mounted to move on the screw body; the screw body comprising a threaded shank of a longitudinal axis AA for anchoring the screw body in a vertebra, and provided at one of its ends with a coupling head for coupling the screw body to the screw head; the screw head comprising a head body of a longitudinal axis BB and through which a channel passes longitudinally that is suitable for receiving, in the head body bottom portion, the coupling head; said vertebral anchor device further comprising assembly means for assembling together the coupling head and the screw head, the coupling head having a portion of cylindrical shape and of axis perpendicular to the threaded shank.

8 Claims, 5 Drawing Sheets

(56) References Cited

U.S. PATENT DOCUMENTS

| | | | |
|---|---|---|---|
| 2006/0089644 A1 | 4/2006 | Felix | |
| 2006/0111715 A1* | 5/2006 | Jackson | A61B 17/861 |
| | | | 128/897 |
| 2007/0043355 A1* | 2/2007 | Bette | A61B 17/7037 |
| | | | 606/250 |
| 2007/0161996 A1* | 7/2007 | Biedermann | A61B 17/7037 |
| | | | 606/305 |
| 2008/0147129 A1* | 6/2008 | Biedermann | A61B 17/7032 |
| | | | 606/308 |
| 2008/0183223 A1* | 7/2008 | Jeon | A61B 17/7038 |
| | | | 606/305 |
| 2009/0076552 A1* | 3/2009 | Tornier | A61B 17/7037 |
| | | | 606/264 |
| 2010/0204735 A1* | 8/2010 | Gephart | A61B 17/7037 |
| | | | 606/264 |
| 2011/0178558 A1* | 7/2011 | Barry | A61B 17/7037 |
| | | | 606/302 |
| 2011/0178559 A1 | 7/2011 | Barry | |
| 2012/0303072 A1* | 11/2012 | Eisermann | A61B 17/7034 |
| | | | 606/305 |
| 2014/0188171 A1* | 7/2014 | Huang | A61B 17/7038 |
| | | | 606/278 |

\* cited by examiner

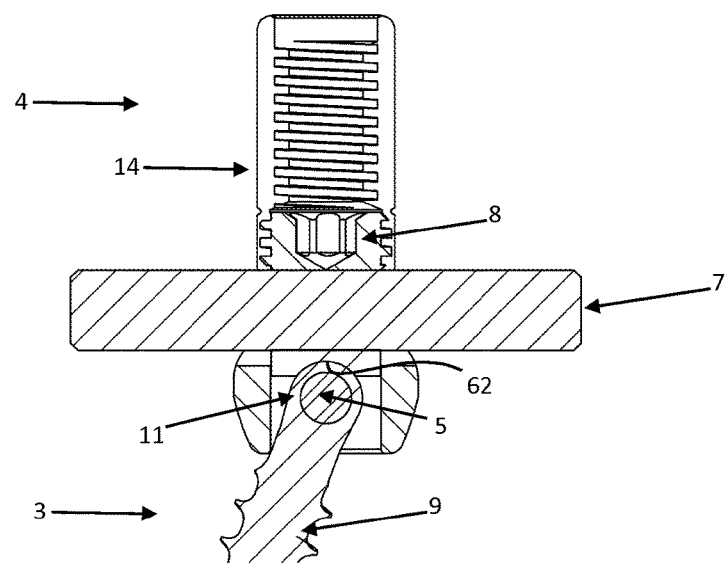
FIG. 5
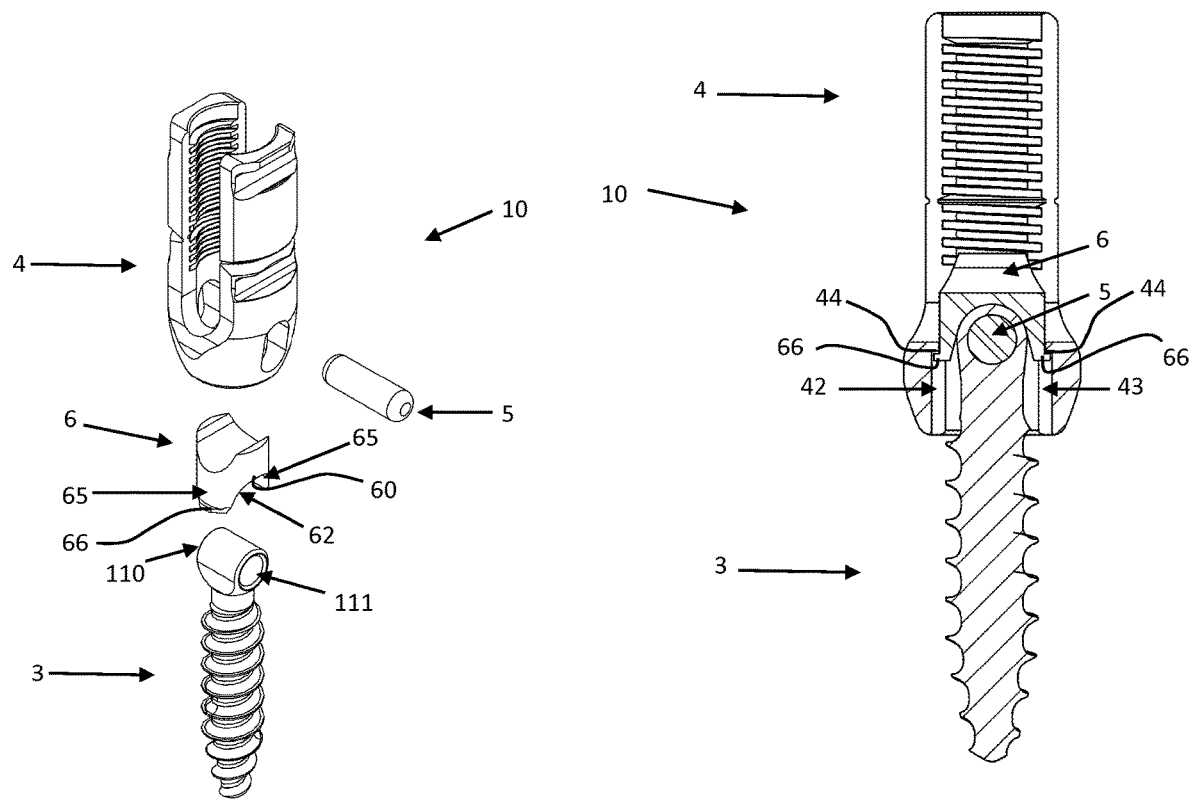
FIG. 6
FIG. 7

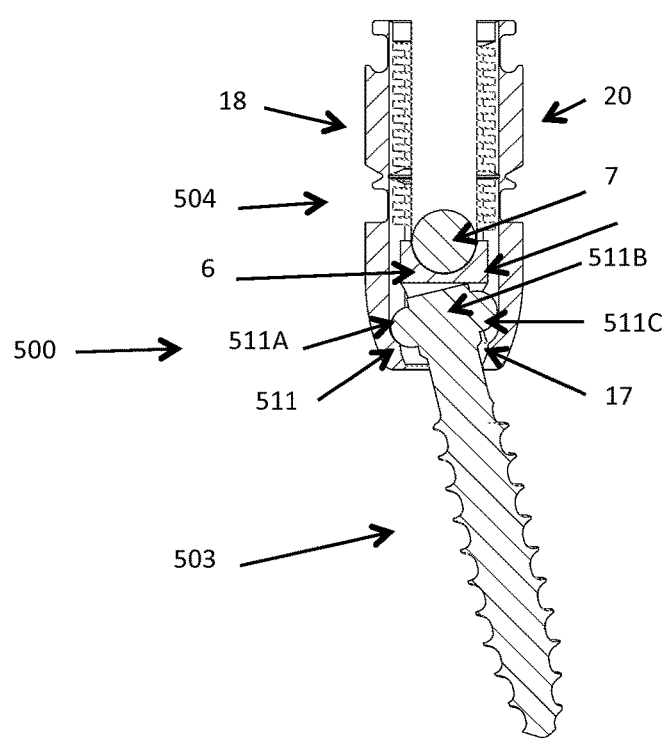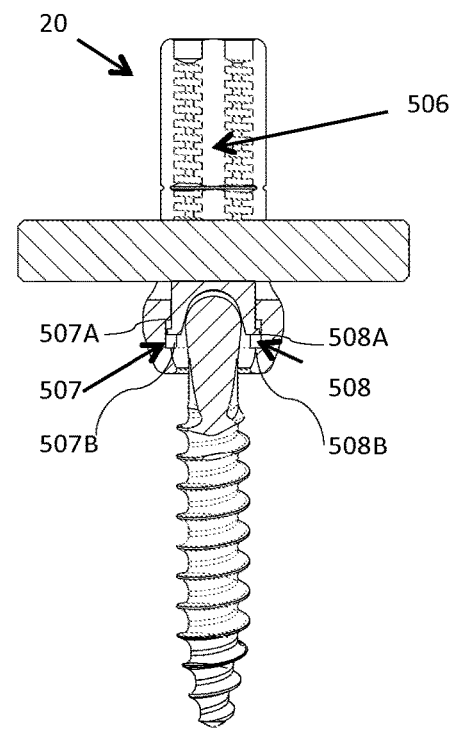
FIG. 8                FIG. 9
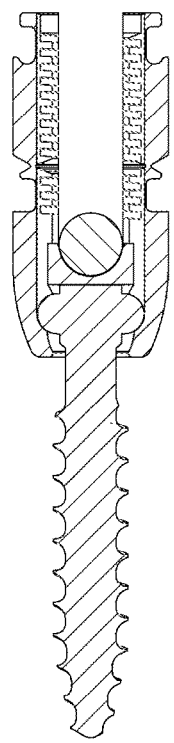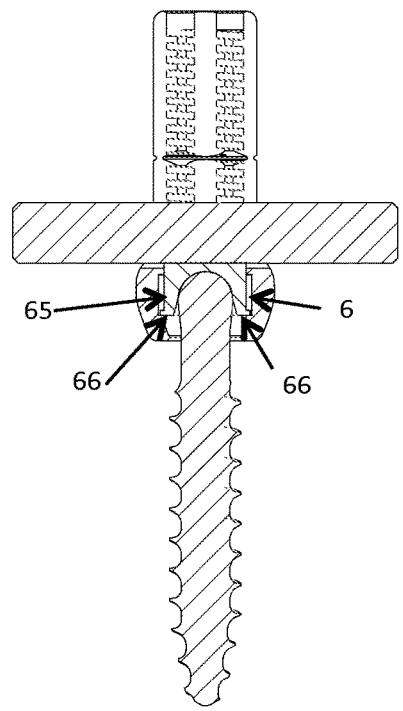
FIG. 10               FIG. 11

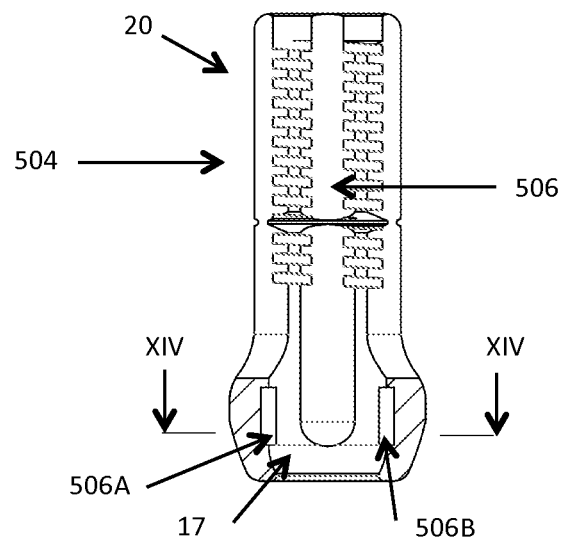
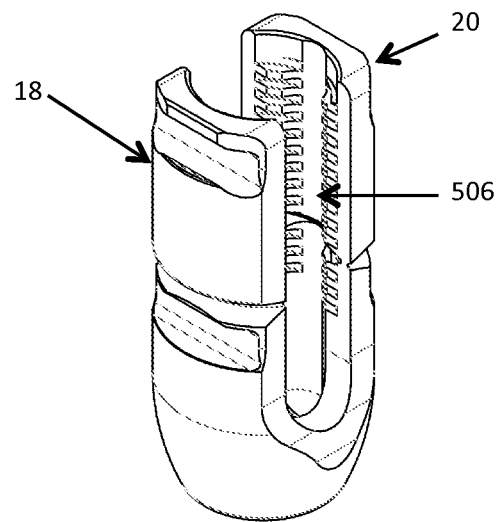
FIG. 12  FIG. 13
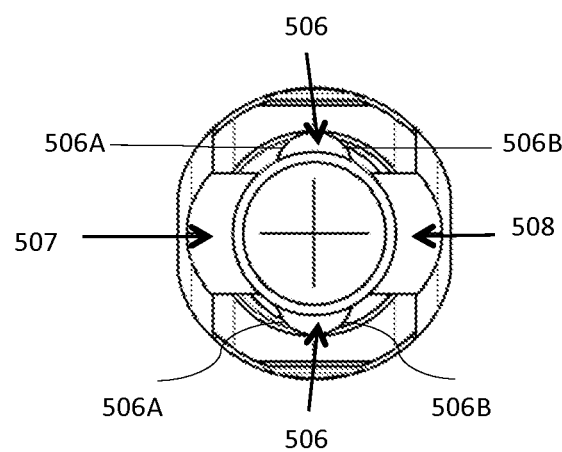
FIG. 14

POLYAXIAL VERTEBRAL ANCHORING DEVICE FOR STRAIGHTENING A VERTEBRA

This application is a 371 national stage application of International Application Number PCT/FR2015/052817 filed Oct. 20, 2015, which claims priority to French Application Number 1460059 filed Oct. 20, 2014.

BACKGROUND

The invention relates to a vertebral anchor device comprising a bone anchor screw having a screw body and a screw head mounted to move on the screw body.

The bone anchor device of the invention is designed particularly but not exclusively for treating curvatures or deviations of the spine, such as scolioses.

Scoliosis is a deviation of the spine whereby the vertebrae define a curvature that is classically S-shaped. It is the consequence of rotation of vertebrae. More specifically, the spine, i.e. the vertebral column, has an inclination in the frontal plane or "coronal plane", it also being possible for the vertebrae affected by the deviation to have a rotation in the horizontal plane or "transverse plane."

To reduce the deviation of the spine, in particular in severe scolioses, the surgical technique of spinal arthrodesis or "spinal fusion" is used. The aim of spinal arthrodesis is to stop the progression of the curvature of the spine and to reduce the spinal deformation by restoring the stability and alignment of the spine.

The spinal deformation is reduced by using bone anchor screws in the vertebrae concerned, and link rods mounted on the bone anchor screws. The bone anchor screws are implanted substantially perpendicularly relative to the vertebrae to which they are fastened, while the link rod should be placed substantially parallel to the spine. A clamping nut is then placed on each head to immobilize the link rod to an extent while nevertheless allowing it to move in rotation and in translation on the head in such a manner as to allow the reduction manipulations to take place before the nut is finally tightened, thereby fully immobilizing the link rod on the head.

Straightening (derotation) of the vertebra is performed either directly during final tightening of the nut when the anchor screws used are fixed-head screws or uniplanar screws, or else prior to final tightening when the anchor screws used are polyaxial screws. When polyaxial screws are used, the straightening is achieved by gradually applying tractions or compressions to each of the bone anchor screws implanted on the vertebrae to be straightened by means of appropriate instruments or by moving the link rods in rotation.

Unfortunately, regardless of whether they are fixed-head screws, uniplanar screws, or polyaxial screws, the anchor screws that are used suffer from drawbacks for implementing spine deformation reduction.

The main drawback encountered with fixed-head anchor screws lies in putting the link rods in place. Depending on the positions of the vertebrae, the respective heads of the various bone anchor screws may have different inclinations and directions due to the various orientations of the vertebrae, so that it is difficult to place a link rod through all of the heads of the anchor screws. It is then necessary to make curvature adaptations to the link rods in order to put them in place in the screw heads, and such an operation is difficult in most situations in which the deformation of the spine is considerable.

Polyaxial-head anchor screws make it possible to overcome the drawbacks of fixed-head anchor screws, since the polyaxial heads can be oriented in all directions in three-dimensional space in order to receive the link rods. However, polyaxial-head anchor screws suffer from the drawback of not making it possible to straighten the vertebrae directly, since the vertebrae remain in place during the final tightening of the nut. It is thus necessary, once the bone anchor elements, the link rod, and the clamping nuts are in place, to reduce the deviation of the vertebrae by techniques of derotating the vertebrae and of bending the link rod. The operation of straightening vertebrae with polyaxial screws thus constitutes a whole separate operation unlike the operation performed with fixed-head screws that is performed jointly with the operation of tightening the nuts.

Uniplanar screws are characterized by moving in a single plane. Although, like fixed-head screws, uniplanar screws allow the vertebrae to be straightened during the operation of tightening the nuts, they only offer limited movement between the screw head and the screw body (movement in a single plane) so that, when the vertebral length to be corrected is large and when it is necessary to use a plurality of anchor screws, the movement in the plane is generally insufficient to enable the link rods to be put in place. It is then necessary, like it is with fixed-head screws, to make curvature adaptations to the link rods.

SUMMARY

An object of the invention is to remedy those problems by proposing a bone anchor device and an associated spine-straightening system that combines the features of fixed-head/uniplanar screws and of polyaxial-head screws. Thus, an object of the invention is to propose a bone anchor device that makes it easier to place the link rods on the bone anchor device and that enables the vertebra in which the device is implanted to be straightened in the coronal plane while also allowing angulation in the sagittal plane.

Another object of the invention is to propose an anchor device that is compact.

To this end, and in a first aspect, the invention provides a vertebral anchor device comprising a bone anchor screw having a screw body and a screw head for coupling a link element to the screw body, the screw head being mounted to move on the screw body, the screw body comprising a threaded shank of longitudinal axis for anchoring it in a vertebra, and provided at one of its ends with a coupling head for coupling it to the screw head, the screw head comprising a head body of longitudinal axis and through which a channel passes longitudinally that is suitable for receiving, in its bottom portion, the coupling head. The device is remarkable in that it further comprises assembly means for assembling together the coupling head and the screw head, said assembly means being arranged in such a manner that after the screw body and the screw head have been assembled together but before the link element is immobilized on the screw head, said assembly means allow a movement in translation of the screw body relative to the screw head parallel to the longitudinal axis BB of the screw body and any movement in rotation of the screw body relative to the screw head to the exclusion of any movement in rotation about the longitudinal axis BB of the screw body, the coupling head having a portion of cylindrical shape and of axis perpendicular to the threaded shank.

Thus, by means of the configuration of the coupling head of the screw body and by means of the connection provided between said screw body and the screw head, a figure-eight movement of the coupling head inside the reception cavity for receiving the screw head is allowed, that movement making it possible to impart to the anchor screw a feature similar to the feature provided by a polyaxial screw while a link element is being inserted, while also making it possible, while the link element is being immobilized on the anchor screw, to straighten up the screw body in the coronal plane, and thus to straighten up the vertebra in which the device is implanted, and while preserving the inclination of the screw head in the sagittal plane.

Advantageously, a key of circular cross-section passes longitudinally through the coupling head, the ends of the key being received in respective associated oblong holes provided in the screw head, each of the oblong holes extending in a direction parallel to the longitudinal axis BB of the head body, the key and the oblong holes forming said assembly means.

Advantageously, at least one of the holes is a through hole.

Advantageously, the key is secured to the coupling head so as to be constrained to move therewith.

In a particular embodiment, the coupling head and the key are formed in one piece.

Advantageously, the portion of cylindrical shape of the coupling head is connected to the threaded shank via a portion of spherical shape.

Advantageously, the device further comprises a cradle-forming part having a bottom surface provided with a bore of shape complementary to the coupling head, and a top surface of concave shape suitable for receiving the link element and extending in a direction perpendicular to the direction in which the bore in the bottom surface extends.

Advantageously, the screw head is provided with longitudinal inside grooves dimensioned to allow the cradle-forming part to move axially. In a particular embodiment, the screw head is provided with two longitudinal inside grooves arranged to enable the cradle-forming part to move axially between a position allowing the screw head to move relative to the screw body and a position locking the screw head to the screw body.

Advantageously, the device further comprises means making it possible to lock the cradle in the channel in a determined longitudinal position.

In another particular embodiment, the portion of cylindrical shape of the coupling head is extended at either end by a respective rounded end portion, each end portion being suitable for being received in a respective longitudinal inside trough provided in the screw head, said inside trough being of shape complementary to the associated end portion. In this configuration, the cradle advantageously constitutes the assembly means.

The invention also provides a spine-straightening system comprising: bone anchor devices, each of which is designed to be implanted in a vertebra and is arranged to receive a link rod, at least one of the bone anchor devices being a device as described above; at least one link rod; and clamping nuts suitable for fastening the link rod to and immobilizing it on each of the anchor devices.

BRIEF DESCRIPTION OF THE FIGURES

Other objects and advantages of the invention appear from the following description given with reference to the accompanying drawings, in which:

FIG. 5 is a view in section in the sagittal plane through the anchor device of FIG. 4;

FIG. 6 is an exploded view of a second embodiment of a vertebral anchor device of the invention;

FIG. 7 is view in longitudinal section through the anchor device of FIG. 6;

FIGS. 8 and 9 are views in section respectively in the coronal plane and in the sagittal plane through a third embodiment of an anchor device of the invention, before the vertebra is straightened;

FIGS. 10 and 11 show respective ones of the anchor devices of FIGS. 8 and 9, after the vertebra has been straightened and the link element has been immobilized by tightening a nut;

FIG. 12 is a view of the screw head of the anchor device of FIG. 9;

FIG. 13 is a side perspective view of the screw head of FIG. 12; and

FIG. 14 is a view in section through the screw head of FIG. 12 on the plane XIV-XIV.

To make the drawings clearer, identical or similar elements in the various embodiments are given identical references in all of the figures.

DETAILED DESCRIPTION

Figure 1:
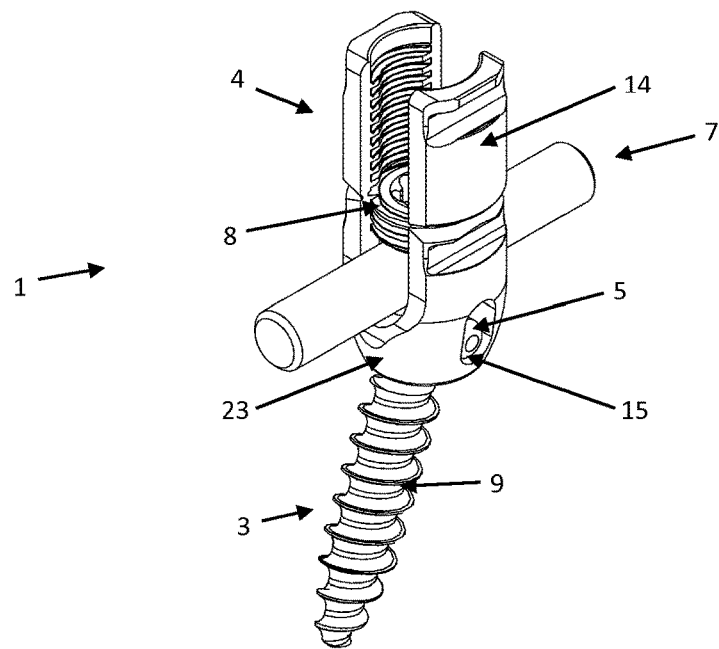
FIG. 1 is a diagrammatic perspective view of a first embodiment of a vertebral anchor device of the invention.
Figure 2:
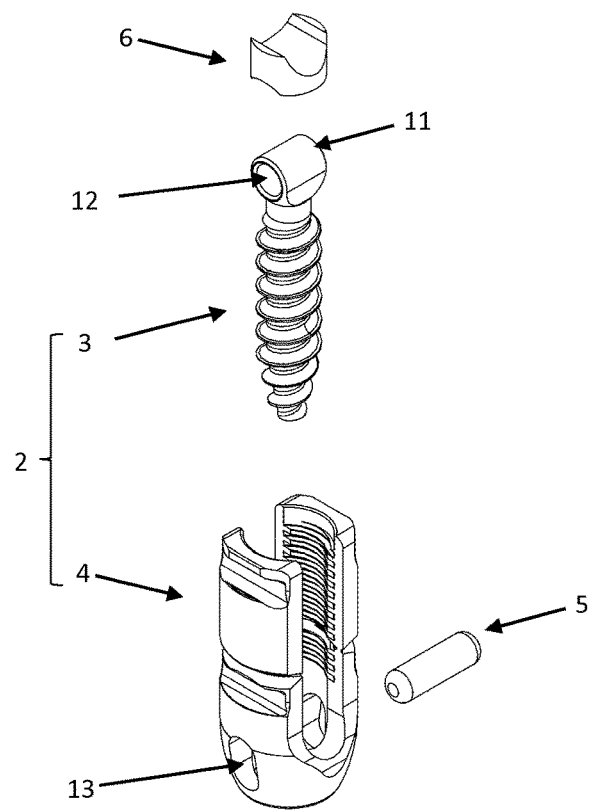
FIG. 2 is an exploded view of the vertebral anchor device of FIG. 1.

With reference to FIGS. 1 to 5, a description follows of a vertebral anchor device 1 that is designed to be connected to other anchor devices via link elements of the link rod type 7, said vertebral anchor devices being fastened to respective vertebrae of the portion of the spine that is affected by the deformation. The resulting assembly thus forms a spine-straightening system.

The anchor device of the invention comprises a bone anchor screw 2 having a screw body 3 provided at one of its ends with a screw head 4 for coupling the link rod 7 to the screw body 3.

The screw body 3 comprises a threaded shank 9 having a longitudinal axis AA and designed to be implanted in the vertebra to be straightened. Said threaded shank 9 is provided at one of its ends 10 with a head 11 configured to enable the threaded rod 9 to be coupled to the screw head 4. That shank head is referred to below as the "coupling head" 11.

The coupling head 11 has a portion 112 of cylindrical outside profile and of axis CC perpendicular to the axis AA of the threaded shank 9. In the embodiment shown, the coupling head 11 is provided with an axial bore 12 that extends from one end of the head to the other and through which a key 5 passes, which key is of a cylindrical shape complementary to the shape of the bore 12. The key 5 is advantageously disposed coaxially with the cylindrical portion 112 of the coupling head 11. The key 5, which has a length greater than the length of the coupling head 11, is disposed in the bore 12 in such a manner as to have ends 50, 51 extending beyond the ends 110, 111 of the coupling head 11 to reach respective ones of the oblong holes 13, 15 provided in the screw head. The key 5 configured in this way connects the coupling head 11 to the screw head 4.

In the embodiment shown, the cylindrical portion 112 of the coupling head 11 is connected to the threaded shank 9 via a portion 113 of spherical outside profile. The advantage of providing such a spherical portion 113 is to improve the polyaxial nature of the screw head 4.

In the embodiment shown, and in known manner, the screw head 4 has a head body 14 of longitudinal axis BB and of tulip shape.

More particularly, the head body 14 is provided longitudinally with a through channel 16 extending between the bottom and top ends 140, 141 of the head body 14. The terms "bottom" and "top" are defined relative to the position of the bone anchor device 1 in the figures. In its top portion, the channel 16 is provided with tapping for receiving a clamping nut 18, and, in its bottom portion, it is provided with a reception cavity 17 for receiving the coupling head 11. As can be understood below, the reception cavity 17 forms a movement chamber within which the coupling head 11 can move.

The head body 14 is also provided with two side arms 18, 20 arranged to define a U-shaped transverse channel designed to receive the link rod 7. The transverse channel, situated above the reception cavity 17, opens out into said cavity. Advantageously, each side arm 18, 20 is provided with a notch 180, 200 for attaching a specific instrument, such as, for example, a guide tube used in minimally invasive surgery.

In the embodiment shown, each of the side arms 18, 20 has a respective longitudinal extension 19, 21. Each arm 18, 20 is connected to one of the extensions 19, 21 by a break zone 22, 24 making it possible to remove the extension once the surgery is finished. This offers the advantage of enabling considerable rod reductions to be made. These break zones 22, 24 are constituted by notches of depth and geometrical shape that are determined to enable a clean break to be obtained when a lateral force exceeding a threshold value is exerted on one of the extensions using a specific instrument. The portion of the channel 16 that is defined by these arms is advantageously tapped. In the same way as for the arms, each extension 19, 21 is advantageously provided with a notch 190, 210 for attaching a specific instrument, such as, for example, a guide tube used in minimally invasive surgery. Such a screw head 4 is designed, in particular, to handle major reductions. Naturally, the anchor screw 1 of the invention is not limited to such an application, and the screw head 4 may be of conventional shape (i.e. not have an extension).

The arms 18, 20 of the screw head 4 are interconnected by a base 23 provided with two oblong holes 13, 15 provided in alignment with said arms and extending in a direction parallel to the longitudinal axis BB of the head body 14. The holes 13, 15 are dimensioned to receive respective ones of the ends 50, 51 of the key 5.

As can be understood below, the key 5 and the oblong holes 13, 15 are arranged such that, before the link rod 7 is immobilized on the screw body 3 under the action of the clamping nut 8, they allow a single movement in translation of the screw head relative to the screw body 3 parallel to the longitudinal axis BB of the channel 16 and any movement in rotation to the exclusion of a movement in rotation about the longitudinal axis BB of the screw body 3. As can be understood from the figures, the movement in translation is limited, the bottom and top surfaces of the holes 13, 15 constituting bottom abutment surfaces 130, 150 and top abutment surfaces 131, 151 against which the coupling head 11 as equipped with the key 5 comes into abutment while it is moving inside the reception cavity 17. The side surfaces of the holes 13, 15 constitute abutment surfaces that prevent any movement in rotation about the axis BB of the head body 14. The holes 13, 15 should be long enough to allow the screw body 3 to move about an axis perpendicular to the axes BB and CC before the nut is tightened onto the link rod. In a particular configuration, the movement in translation may constitute merely axial clearance movement between the screw head 4 and the screw body 3.

The screw body 3 is assembled to the screw head 4 by loading the screw body 3 via the top of the screw head 4. The screw body 3 is placed in the screw head 4 in such a manner as to position the bore 12 of the coupling head 11 in register with the holes 13, 15 in the head body 14. In order to enable the screw head to be adjusted to fit the screw body 3, the coupling head 11 of the screw body 3 is advantageously dimensioned to enable the head body 14 to move in rotation about the axis AA of the threaded shank 9. Thus, the head body 14 can be turned on the screw body 3 until it comes to position the bore 12 in register with the holes 13, 15 in the head body 14.

The key 5 is then inserted into the bore 12 via one of the holes 13, 15 and is pushed into it until the end opposite from the inlet hole comes to be placed in the other hole 15, 13. The key 5 is mounted in the bore 12 in the coupling head 11 by force in order to secure the two parts together and thus in order to limit any risk of the key 5 coming out. Naturally, the two parts can be secured together so that they are constrained to move with each other by implementing any other fastening means (adhesive bonding, welding, etc.) without going beyond the ambit of the invention.

The vertebral anchor device 1 further includes a cradle-forming part 6. In known manner, the cradle-forming part 6, referred to below as the "cradle", has a bottom surface and a top surface that are shaped to receive respectively the coupling head 11 of the screw body 3 and a link rod 7.

Thus, in the embodiment shown, the cradle 6 has a bottom surface 60 provided with a cylindrical bore 62 suitable for co-operating with the coupling head 11, and a concave top surface 64 suitable for receiving the link element 7 and extending in a direction perpendicular to the direction in which the cylindrical shape of the bottom surface extends.

The terms "top" and "bottom" are defined relative to the position of the cradle when it is placed in the screw head 4.

Figure 3:
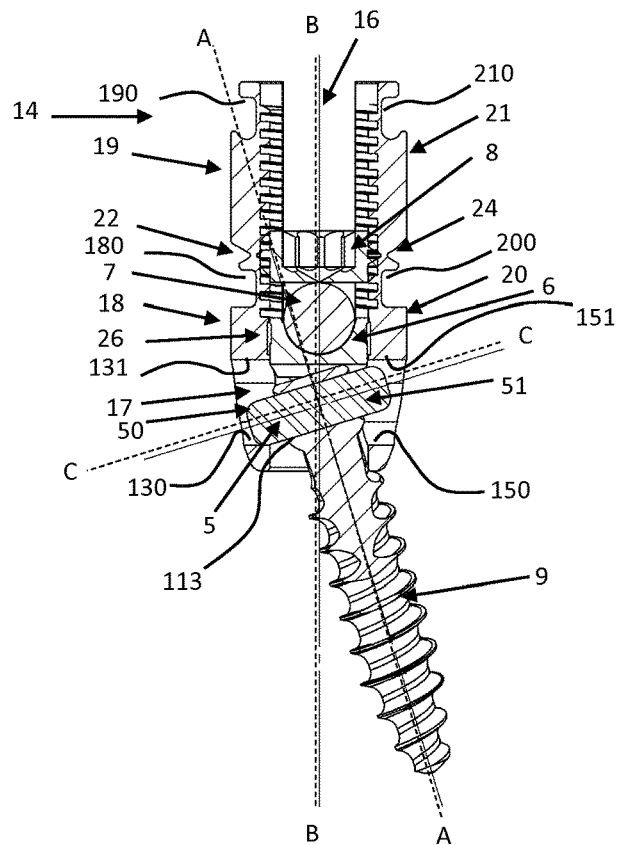
FIG. 3 is a view in section in the coronal plane through the anchor device of FIG. 1 before the vertebra is straitened.
Figure 4:
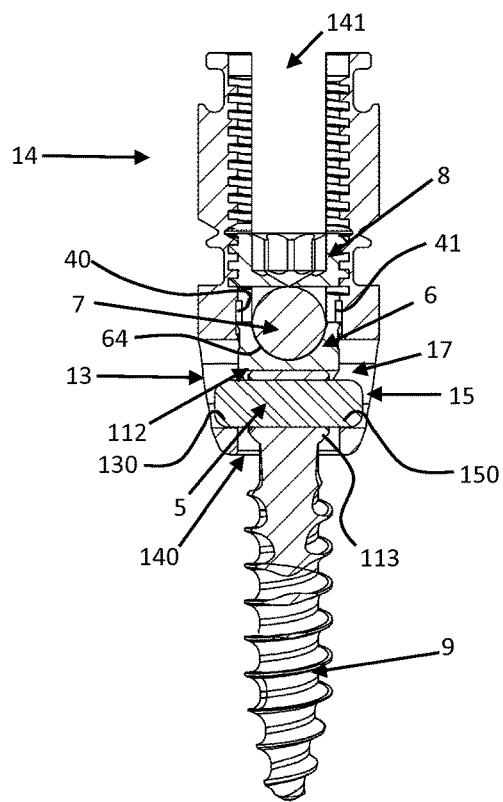
FIG. 4 shows the anchor device of FIG. 3 after the vertebra has been straightened and the link element has been immobilized by tightening the nut.

As shown in FIGS. 3 to 5, the cradle 6 is received in a reception cavity 26 provided in the head body 14, at the end wall of the U-shape of the arms 18, 20. The reception cavity opens out into the reception cavity 17 for receiving the coupling head 11. The reception cavity 26 is advantageously provided with two longitudinal inside grooves 40, 41 that are dimensioned to enable the cradle 6 to move axially between a position allowing the screw head 4 to move relative to the screw body 3 (high position of the cradle) and a position locking the screw head 4 to the screw body 3 once the link rod 7 has been immobilized by the clamping nut (low position of the cradle). In the embodiment shown, the grooves are provided in alignment with respective ones of the oblong holes 13, 15 in the head body 14.

Advantageously, the outside surface of the coupling head 11 and the bottom surface 60 of the cradle 6 are provided with striations or serrations. This makes it possible to prevent any movement of the screw head 4 on the screw body 3 once the nut has been tightened.

FIGS. 3 to 5 shows how the component elements of the bone anchor device 1 are positioned relative to one another before and after tightening of the nut.

Thus, FIG. 3 shows an example of positioning of the device 1 on the vertebra to be straightened. In this example, the screw head 4 and the screw body 3 are inclined relative to the coronal and sagittal planes. In this position, the end 50 comes into abutment against the bottom abutment surface 130 of the hole 13 while the end 51 comes into abutment against the top abutment surface 151 of the hole 15.

Under the action of the tightening of the nut (movement of the clamping nut 8 downwards), the cradle 6 is moved in translation along the grooves 40, 41, towards the bottom opening in the head body 14. While it is moving, the cradle 6 enters the reception cavity 17 for receiving the coupling head 11, so as to come into contact with the top portion of the coupling head 11 and so as to exert a pressing force thereon until the screw head 4 is brought into a position in which the ends 50, 51 rest on the bottom abutment surfaces 130, 150 of the holes 13, 15 (FIGS. 4 and 5). During this action, the coupling head 11, and therefore the threaded shank 9 fastened in the vertebra, is subjected to a movement in rotation such that the screw body 3 is realigned in the coronal plane, while also preserving the previously given inclination of the screw head 4 in the sagittal plane.

In the embodiment shown, the holes 13, 15 in the screw head 4 that are designed to co-operate with the ends of the key 5 are through holes. Naturally, the invention is not limited to this configuration of screw head 4 and a configuration may be provided in which only one of the holes is a through hole so as to enable the key 5 to be inserted into the axial bore in the coupling head 11, the other hole being blind.

Similarly, in the above-described embodiment, the key and the coupling head 11 are constituted by two independent parts. In an advantageous embodiment, provision may be made for the coupling head 11 and the key 5 to be formed in one piece. In which case, the screw head 4 is arranged to enable the screw body 3 and the screw head 4 to be assembled together laterally. In this configuration, one of the holes opens out into the bottom end 140 of the head body 4. Similarly, provision may be made for the screw head to be provided merely with one through oblong hole opening out in the second end 140 of the head body 4, it being possible for the other hole to be a blind oblong hole.

FIGS. 6 and 7 show an anchor device 10 in which its component elements (screw head, threaded shank, and cradle) are assembled together via the base of the screw head. The anchor device 10 has substantially the same characteristics as the above-described anchor device 1. Only the additional or changed characteristics relating to the anchor device 10 and to assembly thereof are described below.

In this embodiment, the cradle 6 has bottom extensions that co-operate with the bottom surface 60 to define the cylindrical bore 62. At its end, each of said extensions 65 is provided with a respective outwardly extending retaining catch 66. "Outwardly extending" is used to mean that the catch extends away from the cylindrical bore 62.

As regards the screw head 4, upstream from the reception cavity 17 for receiving the coupling head 11, the channel 16 is provided with two symmetrical longitudinal grooves 42, 43 that extend to the bottom end 140 of the screw head 4. Each groove 42, 43 co-operates with the reception cavity 17 in the coupling head 11 to define a shoulder 44 against which one of the retaining catches 66 of the cradle 6 comes into abutment when the screw body 3 and the cradle 6 are loaded in the screw head 4 via its bottom end.

The shoulders 44 and the retaining catches 66 thus form means making it possible to lock the cradle 6 in the channel 16 in a determined longitudinal position, thereby avoiding any untimely withdrawal of the cradle during mounting of the screw head 4 on the screw body 3 as can occur in the above-described embodiment. This configuration also offers the advantage of retaining the screw head 4 on the screw body 3 even before the key 5 is mounted into the coupling head 11, thereby making it easier for the screw head 4 and the screw body 3 to be assembled together.

Naturally, the means implemented to lock the cradle 6 in the channel 16 in a given longitudinal position that are shown in FIG. 7 and that are described above are given by way of example, and other arrangements and means may be provided for defining a longitudinal abutment for the cradle in the channel without going beyond the ambit of the invention. In particular, a cradle may be provided in which the retaining catches 66 are provided at the top extensions of the cradle, the position of the shoulder 44 in the channel 16 being adapted for that purpose.

FIGS. 8 to 14 show another embodiment of an anchor device 500 of the invention. In this embodiment, instead of being assembled together by means of a key mounted through the coupling head and through the oblong holes in the screw head 4, the coupling head and the screw head are assembled together by means of a cradle and of a particular configuration of the coupling head and of the screw head.

More particularly, the coupling head (referenced 511) includes a cylindrical portion 511B extended at either end by a rounded end portion 511A, 511C.

The cradle 6 implemented in the anchor device 500 is provided with a bottom bore having a shape complementary to the cylindrical portion 511B of the coupling head 511. In the same way as for the cradle of the second embodiment shown in FIG. 6, the cradle 6 has bottom extensions 65 that define the bottom bore and that are provided with respective outward retaining catches 66. The top extensions that define the bore designed to receive the link rod 7 are preferably not provided with catches.

The screw head (referenced 504) has all of the characteristics of the screw head 4 of the above-described embodiments. In the embodiment being described, the screw head 504 is provided with two inside troughs 506 of shape complementary to the end portions 511A, 511C of the coupling head 511. Said troughs extend longitudinally from the top ends of the side arms 18, 20 to into the reception cavity 17 for receiving the coupling head 511 (FIG. 12). The troughs 506 are of depth such that the distance between the end walls of them is slightly greater than the length of the coupling head (length between the vertices or tips of the two end portions). A distance that is "slightly greater" means a distance sufficient to give a small amount of clearance to the coupling head 511 when said coupling head is received in the reception cavity 17. Configured in this way, the two inside troughs 506 enable the coupling head 511 to pass while the screw body 503 is being loaded via the top of the screw head 504 while preventing movement in rotation of the screw body 503 about the axis BB (movement prevented by the end portions 511A, 511C being put into abutment against the side edges 506A, 506B of the troughs 506).

The reception cavity 17, provided in the screw head 504 and designed to receive the coupling head 511 of the screw body 503, is also provided with two inside longitudinal grooves 507, 508, each of which is situated below the end wall of the U-shape of a respective one of the transverse channels for receiving the link rod 7. The grooves 507, 508 thus have an angular offset of about 90° relative to the longitudinal troughs 506 (FIG. 14). The grooves 507, 508 are dimensioned to receive the bottom extensions 65 of the cradle 6 and to enable said cradle to move axially in the reception cavity 17. Each of the grooves 507, 508 is defined by a top shoulder 507A, 508A and by a bottom shoulder 507B, 508, against which shoulders the retaining catches 66 of the cradle 6 come into abutment. The top shoulders 507A, 508A and the bottom shoulders 507B, 508B respectively define a high position and a low position for the cradle 6.

It can thus be understood that once the screw body 503 is loaded into the screw head 504 and once the cradle 6 is placed in the reception cavity 17 above the coupling head 511, the screw head 504 is held assembled to the screw body 503 by the cradle 6. Before the link rod 7 is immobilized by tightening the nut, the cradle 6 is free to move in translation in the reception cavity 17, between the high position and the low position. The screw head 504 can thus move in translation on the screw body 503 along the axis BB. The movement in rotation of the screw body 503 relative to the screw head, apart from the movement in rotation of the screw head 504, is allowed due not only to the fact that the cradle 6 is movable, but also due to the way the end portions 511A, 511C of the coupling head 511 are arranged in the inside troughs 506 of the cavity 17 in which the coupling head 511 is received. FIGS. 8 and 9 show the anchor device 500 in which the cradle 6 is free to move in translation between the low position and the high position. While the nut is being tightened onto the link rod 7 until it is fully tightened, the cradle 6 is driven into its low position so as to be locked in that position once the nut is fully tightened. FIGS. 10 and 11 show the cradle 6 as locked in the low position after final tightening of the clamping nut (camping nut not shown in this embodiment but shown in FIGS. 1 to 5).

The invention is described above by way of example. Naturally, the person skilled in the art can implement various variant embodiments of the invention without going beyond the ambit of the invention.

The invention claimed is:

1. A vertebral anchor device comprising a bone anchor screw having a screw body and a screw head for coupling a link element to the screw body, the screw head being mounted to move on the screw body;
    the screw body comprising a threaded shank defining a longitudinal axis for anchoring the screw body in a vertebra, and provided at one of its ends with a coupling head for coupling the screw body to the screw head;
    the screw head comprising a head body defining a longitudinal axis and through which a channel passes longitudinally that is suitable for receiving, in a head body bottom portion, the coupling head;
    said vertebral anchor device further comprising assembly means for assembling together the coupling head and the screw head, said assembly means being arranged in such a manner that after the screw body and the screw head have been assembled together, but before the link element is immobilized on the screw head, said assembly means allow a movement in translation of the screw body relative to the screw head parallel to the longitudinal axis of the screw body, and any movement in rotation of the screw body relative to the screw head except in rotation about the longitudinal axis of the screw, the coupling head having a portion of a cylindrical shape defining an axis perpendicular to the threaded shank; wherein a key of circular cross-section passes longitudinally through the coupling head, the ends of the key being received in respective associated oblong holes provided in the screw head, each of the oblong holes extending in a direction parallel to the longitudinal axis of the head body, the key and the oblong holes forming said assembly means.

2. The vertebral anchor device according to claim 1, wherein at least one of the holes is a through hole.

3. The vertebral anchor device according to claim 2, wherein the key is mounted in a secured manner in the coupling head so as to be constrained to move therewith.

4. The vertebral anchor device according to claim 1, wherein the portion of cylindrical shape of the coupling head is extended at either end by a respective rounded end portion, each end portion being suitable for being received in a respective longitudinal inside trough provided in the screw head and of shape complementary to the associated end portion.

5. The vertebral anchor device according to claim 1, wherein the device further comprises a cradle-forming part having a bottom surface provided with a bore of shape complementary to the coupling head, and a top surface of concave shape suitable for receiving the link element and extending in a direction perpendicular to the direction in which the bore in the bottom surface extends.

6. The vertebral anchor device according to claim 5, wherein the screw head is provided with longitudinal inside grooves dimensioned to allow the cradle-forming part to move axially.

7. The vertebral anchor device according to claim 5, further comprising means making it possible to lock the cradle in the channel in a determined longitudinal position.

8. A spine-straightening system comprising:
    bone anchor devices, each of which is designed to be implanted in a vertebra and is arranged to receive a link rod, at least one of the bone anchor devices being a device according to claim 1;
    at least one link rod; and
    clamping nuts suitable for fastening the link rod to and immobilizing it on each of the anchor devices.

* * * * *